United States Patent [19]

Ross et al.

[11] 4,253,201

[45] Mar. 3, 1981

[54] PROSTHESIS WITH SELF-SEALING VALVE

[76] Inventors: David A. Ross, 46 E. Oak St., Chicago, Ill. 60611; Steven M. Aperavich, 4515 N. Green Bay Rd., Racine, Wis. 53404

[21] Appl. No.: 41,981

[22] Filed: May 24, 1979

[51] Int. Cl.³ .............................................. A61F 1/03
[52] U.S. Cl. .................................................. 3/36; 3/1
[58] Field of Search ......................... 3/36, 1; 128/274; 46/90; 272/DIG. 1; 273/65 C, 65 D

[56] References Cited

U.S. PATENT DOCUMENTS

| | | | |
|---|---|---|---|
| 1,758,625 | 5/1930 | Saul | 273/65 D |
| 1,878,715 | 9/1932 | Saul | 273/65 D |
| 2,621,334 | 12/1952 | O'Hare | 273/65 C |
| 3,310,051 | 3/1967 | Schulte | 128/216 |
| 3,527,220 | 9/1970 | Summers | 128/273 X |
| 3,600,718 | 8/1971 | Boone | 3/1 X |
| 3,640,269 | 2/1972 | Delgado | 128/260 X |
| 3,730,186 | 5/1973 | Edmunds, Jr. et al. | 128/325 |
| 3,783,868 | 1/1974 | Bokros | 128/348 X |
| 3,919,724 | 11/1975 | Sanders et al. | 3/36 |
| 4,065,816 | 1/1978 | Sawyer | 3/1 X |

FOREIGN PATENT DOCUMENTS 22019 of 1907 United Kingdom .................. 273/65 D

*Primary Examiner*—Clifford D. Crowder
*Attorney, Agent, or Firm*—Quarles & Brady

[57] ABSTRACT

An inflatable, implantable prosthesis includes a flexible, inflatable, thin wall container of physiologically acceptable material provided with a self-sealing valve assembly which permits fluid to be introduced into or removed from said container to inflate or deflate the prosthesis. The self-sealing valve assembly includes a top having an outer wall and an inner wall which are sealed about their periphery to form an envelope which is filled with a self-sealing gel. The outer wall of the top is secured to the inside of the container and a side wall depends from the top and is connected to a bottom to define a chamber. The chamber has at least one opening in the bottom or side wall so that inflating fluid can pass to and from said chamber into the interior of the container. When inflating or deflating the container, the valve is opened by passing a needle through the envelope and self-sealing gel into the chamber; fluid is removed from or added to the container through the needle or a replacement catheter via the chamber. The chamber shields and protects the thin wall of the container from potentially damaging contact with the needle. The side walls of the chamber are comprised of a flexible material which permits the chamber to collapse to form a more compact uninflated container that may be implanted using a minimum size incision and which expands after implantation.

4 Claims, 5 Drawing Figures

U.S. Patent        Mar. 3, 1981        4,253,201
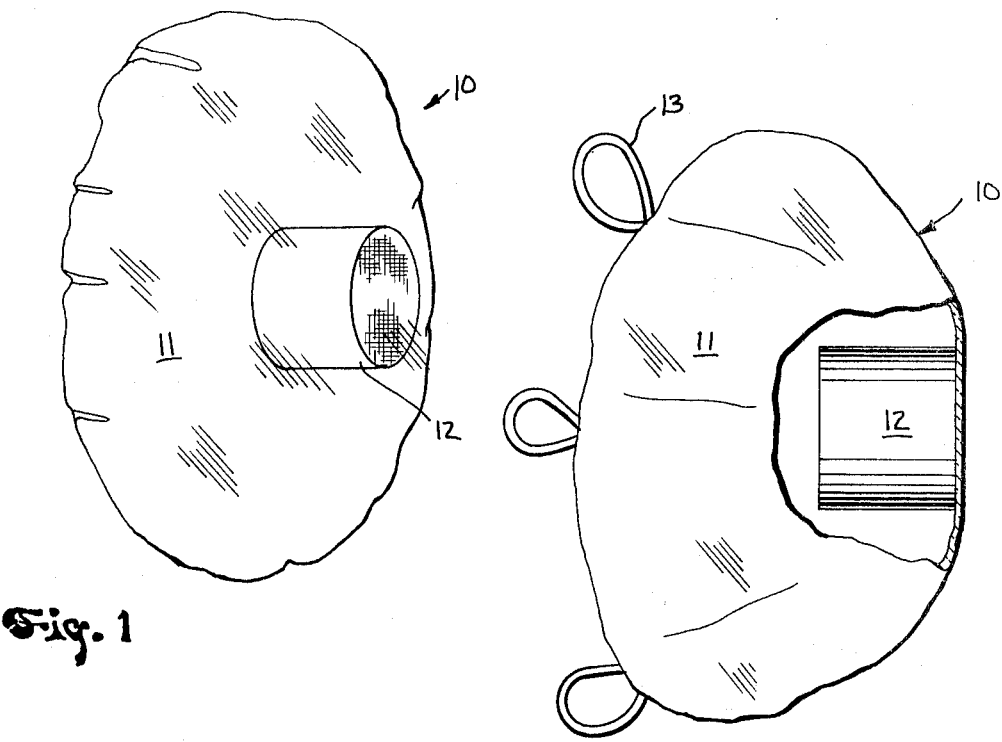
Fig. 1
Fig. 2
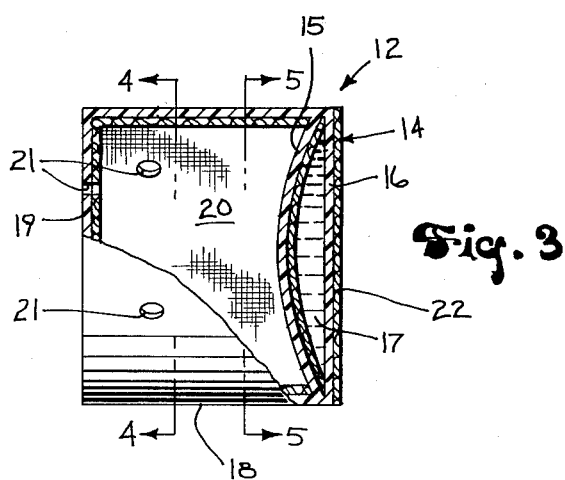
Fig. 3
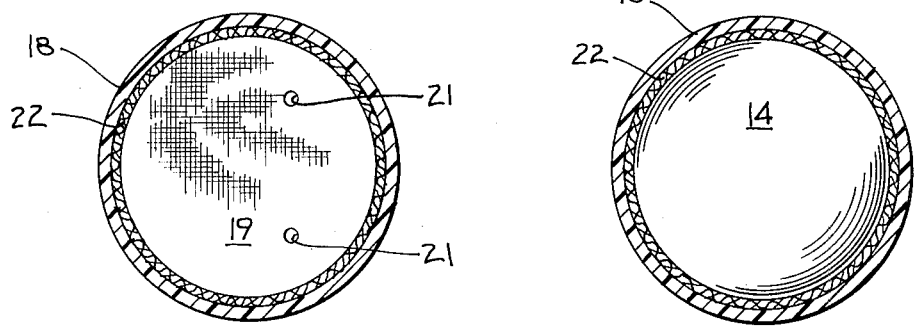
Fig. 4
Fig. 5

PROSTHESIS WITH SELF-SEALING VALVE

TECHNICAL FIELD

The present invention relates generally to the field of inflatable, implantable prostheses and more particularly to prostheses with valves permitting the implanted prostheses to be inflated or deflated after implantation.

BACKGROUND OF THE INVENTION

An inflatable prosthesis for implantation in breast reconstruction or breast augmentation procedures is usually a thin wall container of a physiologically acceptable material such as silicone rubber. The container is preferably equipped with a valve that permits fluid to be introduced into or removed from the container after it has been implanted.

A prosthesis equipped with a particularly suitable valve is disclosed in U.S. Pat. No. 3,919,742. The valve of the patent comprises a double walled envelope which contains a self-sealing silicone gel. The envelope is secured to the inside wall of the container of the prosthesis. The container is inflated by passing a needle through the outer container wall, both of the walls of the envelope and the self-sealing gel to provide communication with the interior of the container. Inflating fluid is then introduced into the interior of the container through the needle or a replacement catheter. The valve of the patent functions extremely well; however, when the prosthesis is completely deflated, the wall of the container behind the valve could be damaged by the piercing needle causing the implated prosthesis to leak.

SUMMARY OF THE INVENTION

The present invention relates to an inflatable, implantable prosthesis which includes a flexible, inflatable, thin wall container of physiologically acceptable material provided with a self-sealing valve assembly which permits fluid to be introduced into or removed from said container to inflate or deflate the prosthesis. The self-sealing valve assembly includes a top having an outer wall and an inner wall which are sealed about their periphery to form an envelope which is filled with a self-sealing gel. The outer wall of the top is secured to the inside of the container and a side wall depends from the top and is connected to a bottom to define a chamber. The chamber has at least one opening in the bottom or the side wall so that inflating fluid can pass to and from said chamber into the interior of the container. When inflating the container, the valve is opened by passing a needle through the envelope walls and the self-sealing gel into the chamber; inflating fluid is then added to the container through the needle or a replacement catheter via the chamber. The side wall and bottom of the chamber help to protect the thin wall of the container from potentially damaging contact with the needle.

In a preferred embodiment, the bottom wall of the chamber is reinforced to provide greater resistance to the passage of a needle than the thin wall of the container.

In another preferred embodiment, the prosthesis also includes suture loops or tabs for anchoring the prosthesis so that it does not move to make the valve inaccessible.

It is the general object of the present invention to disclose an inflatable, implantable prosthesis with a self-sealing valve assembly which makes it unlikely that the thin wall of the container of the prosthesis will be damaged by a needle being used to operate the valve to inflate or deflate the prosthesis.

This and other objects will be apparent from the description which follows.

BRIEF DESCRIPTION OF THE DRAWINGS

FIG. 1 is a perspective view of an inflatable prosthesis incorporating the valve assembly of the present invention;

FIG. 2 is a side view partially in section of the prosthesis of FIG. 1;

FIG. 3 is a side elevational view of an embodiment of the valve assembly partially in section;

FIG. 4 is a bottom view of the valve assembly of FIG. 3; and

FIG. 5 is a top view of the valve assembly of FIG. 3.

DESCRIPTION OF THE PREFERRED EMBODIMENT

In FIG. 1 of the drawing, an inflatable, implantable prosthesis 10 is shown which includes a flexible, thin wall container 11 having a valve assembly 12. The container 11 is formed from a medical application silicone rubber, such as that disclosed in U.S. Pat. No. 3,665,520, which preferably has a low modulus, but high ultimate tensile and tear strength.

As seen in FIGS. 1 and 2, the valve assembly 12 is located within the interior of the container 11 and it is located on the inside wall in the center of the front of the container 11. The center front position is preferred for a prosthesis designed for breast reconstruction. However, if desired, the valve assembly 12 can be located in other positions, such as at the lower end of the container 11.

As seen only in FIG. 2, the prosthesis 10 is further provided with suture loops 13 which are attached to the back of the container and are used to anchor the prosthesis 10 to the chest wall to prevent it from changing positions after implantation.

In FIG. 3, the valve assembly 12 is seen to include a top 14 which has an inner wall 15 and outer wall 16 which are sealed about their periphery to form an envelope which contains a self-sealing silicone gel 17 of the type described in U.S. Pat. No. 3,919,724. The gel is self-sealing as it possesses liquid flow characteristics and it flows to close an opening formed by a needle once the needle has been withdrawn.

The outer wall 16 of the top 14 of the valve assembly 12 is secured directly to the inside wall of the container 11, preferably with a suitable silicone adhesive.

Returning to FIG. 3, the valve assembly 12 can be seen to also include a side wall 18 that depends from the top and is connected to a bottom 19 to form a chamber 20. As seen in FIGS. 3, 4, and 5, respectively, the side wall 18 and bottom 19 are provided with openings 21 extending therethrough, and the top is imperforate. The openings 21 connect the interior of the chamber 20 and the interior of the container 11 permitting fluid to be introduced into the chamber 20 to inflate the container 11 and permitting fluid to be withdrawn from the chamber 20 to deflate the container 11.

In the embodiment seen in the drawings, the walls of the chamber 20 are formed of a mesh 22 embedded in silicone. The mesh reinforces and strengthens the silicone material and it provides a tough needle resistant barrier which prevents a needle which is inserted through the top wall and self-sealing valve into the chamber 20 from encountering the thin wall of the container 11. The mesh reinforced wall and bottom provide substantially greater resistance to the passage of a needle and when encountered, signals a person inflating or deflating the prosthesis that the needle should be relocated in the chamber to avoid penetrating the side wall or bottom and nicking the thin wall of the container 11.

Although the chamber 20 is preferably cylindrical in shape as shown in the drawings, other shaped chambers can be employed, if desired.

In addition to providing resistance to the easy passage of the needle the heavier mesh reinforced side wall and bottom keep the thin wall of a completely deflated container from forming folds immediately behind the self-sealing valve, where it can be nicked or damaged by an inflating needle.

If desired, means can be included for locating the valve after implanting it in the body. Such means could be a radio-opaque material which is added to the gel or valve assembly. Normally, however, the valve can be located by a manipulation.

The prosthesis 10 shown in the drawing is particularly suitable for breast reconstruction and it can be implanted immediately after tissue removal. The suture loops 13 provide convenient means of anchoring the prosthesis to the chest wall to prevent it from rotating and making the valve inaccessible through the skin. Once the prosthesis has been secured in place it is partially filled to a desired level, and the breast reconstructed using plastic surgery. The position of the valve on the inside center front of the container facilitates the use of sequential incremental fillings of the prosthesis to stretch the skin to accommodate a prosthesis of desired volume without impairing the blood supply to the area.

In another embodiment especially useful where it is desired to use the minimum size incision to implant the prosthesis, the side wall is preferably made of unreinforced dacron mesh. The side wall 18 of such a prosthesis can be collapsed to form a more compact uniflated prosthesis. A needle inserted through the self-sealing valve passes through the walls 15,16 of the top 14, through the self-sealing gel 17, contacts the bottom 19 and extends the side wall 18 of the chamber 20 before passing through the reinforcing mesh of the bottom 19. The inflating fluid introduced through the needle or a replacement catheter enters the chamber and passes through the openings in the mesh to inflate the container.

It will be understood that although the invention has been described in connection with a prosthesis particularly adapted for breast reconstruction the same type of valve assembly can be advantageously employed with a prosthesis intended for other uses, e.g., mammary augmentation. A prosthesis for mammary augmentation might have the valve assembly 12 located at the lower end of the prosthesis to facilitate the introduction of the prosthesis in a rolled up condition through a small incision under the breast in the manner described in U.S. Pat. No. 3,919,724.

It will be readily apparent to those skilled in the art that a number of modifications and changes can be made without departing from the spirit or scope of the present invention. For example, in place of the fabricated shielding chamber which is shown in the drawings and has been described, a molded chamber could be used in combination with the double walled self-sealing top piece. Therefore, it is to be understood that the invention is not to be limited by the foregoing description which was for purposes of illustration, but only by the claims which follow.

We claim:

1. In an inflatable, implantable prosthesis which comprises a flexible, inflatable thin walled container and a self-sealing valve on said container so that fluid can be introduced into said container to inflate or deflate said container, the improved valve which comprises a double walled top having a self-sealing gel deposited in the space between the walls, said top being secured to the inside of the container wall, a side wall depending from said top, and a bottom, said side wall connecting the top and the bottom and defining a fluid receiving chamber having at least one opening therein, said side wall being comprised of a flexible material which permits said fluid receiving chamber to be collapsible to form a more compact uninflated container that may be implanted using a minimum size incision and which expands after implantation so that fluid can pass to and from said chamber into the interior of the container.

2. The valve of claim 1 in which the bottom is reinforced and provides increased resistance which signals the user when the tip of the needle has encountered the bottom.

3. The valve of claim 1 in which both the side wall and bottom provide increased resistance which signals the user when the tip of the needle has encountered either.

4. The valve of claim 1 in which the side wall and bottom are reinforced with mesh.

* * * * *